US012357411B2

(12) United States Patent
Koclanes et al.

(10) Patent No.: US 12,357,411 B2
(45) Date of Patent: *Jul. 15, 2025

(54) SYSTEM AND METHODS FOR PROVIDING INDUCTIVE SENSING OF SHARPS AND OTHER MEDICAL INSTRUMENTS

(71) Applicant: Magvation, LLC, Las Vegas, NV (US)

(72) Inventors: Michael P. Koclanes, Johnstown, CO (US); Bill Brown, Chandler, AZ (US); Lakmal Wijesekara, Superior, CO (US); Jason Howe, Fallbrook, CA (US); Niren Angle, Danville, CA (US); Jon Robinson, Elm Grove, WI (US); Paul Gallese, Solon, OH (US)

(73) Assignee: Magvation, LLC, Las Vegas, NV (US)

( * ) Notice: Subject to any disclaimer, the term of this patent is extended or adjusted under 35 U.S.C. 154(b) by 620 days.

This patent is subject to a terminal disclaimer.

(21) Appl. No.: 17/491,829

(22) Filed: Oct. 1, 2021

(65) Prior Publication Data

US 2022/0104903 A1    Apr. 7, 2022

Related U.S. Application Data

(60) Provisional application No. 63/195,924, filed on Jun. 2, 2021, provisional application No. 63/086,300, filed on Oct. 1, 2020.

(51) Int. Cl.
*A61B 90/00* (2016.01)
*A61B 50/36* (2016.01)
*G16H 40/67* (2018.01)

(52) U.S. Cl.
CPC ............ *A61B 90/08* (2016.02); *A61B 50/362* (2016.02); *G16H 40/67* (2018.01); *A61B 2090/0803* (2016.02)

(58) Field of Classification Search
None
See application file for complete search history.

(56) References Cited

U.S. PATENT DOCUMENTS

| 5,227,765 A | 7/1993 | Ishizuka et al. |
| 5,918,739 A | 7/1999 | Bilof et al. |

(Continued)

FOREIGN PATENT DOCUMENTS

| CN | 2257176 | 7/1997 |
| CN | 2887266 | 4/2007 |

(Continued)

OTHER PUBLICATIONS

International Search Report and Written Opinion of the International Searching Authority; PCT/US2021/053131; dated Jan. 10, 2022.

(Continued)

*Primary Examiner* — Devin C Hein

(74) *Attorney, Agent, or Firm* — Jones Day

(57) ABSTRACT

Systems and methods are provided for a surgical needle counting system for an operating room. A system includes counting apparatus and a removable collecting enclosure positioned at an exit of the counting apparatus. The counting apparatus includes a sensor for sensing a surgical needle when it is dropped into the counting apparatus, and the counting apparatus is configured for storing a number of counted surgical needles.

21 Claims, 15 Drawing Sheets

(56) References Cited

U.S. PATENT DOCUMENTS

| | | |
|---|---|---|
| 8,105,296 B2 | 1/2012 | Morris et al. |
| 2004/0193225 A1 | 9/2004 | Esler |
| 2006/0218002 A1 | 9/2006 | Mallett et al. |
| 2008/0061064 A1 | 3/2008 | Michaels |
| 2008/0195247 A1* | 8/2008 | Mallett .................. G07F 11/62 |
| | | 700/231 |
| 2008/0312852 A1 | 12/2008 | Maack |
| 2009/0317002 A1 | 12/2009 | Dein |
| 2010/0155400 A1* | 6/2010 | Finnestad ............ A61B 50/362 |
| | | 524/506 |
| 2012/0173287 A1* | 7/2012 | Cowand ................. G16H 20/10 |
| | | 705/3 |
| 2013/0088354 A1 | 4/2013 | Thomas |
| 2013/0175983 A1 | 7/2013 | Partovi et al. |
| 2014/0374294 A1* | 12/2014 | Joyce ..................... A61B 50/36 |
| | | 206/363 |
| 2015/0168207 A1 | 6/2015 | Pollock et al. |
| 2015/0253055 A1* | 9/2015 | Tsui .......................... B62B 1/12 |
| | | 280/655 |
| 2015/0351850 A1 | 12/2015 | McElhinny et al. |
| 2015/0352259 A1 | 12/2015 | Rooijmans et al. |
| 2019/0190897 A1 | 6/2019 | Rosenberg et al. |
| 2020/0013191 A1* | 1/2020 | Berning ................. A61B 50/24 |

FOREIGN PATENT DOCUMENTS

| | | | |
|---|---|---|---|
| CN | 201906004 | | 7/2011 |
| CN | 201410036254 | | 1/2014 |
| CN | 103767790 | | 5/2014 |
| CN | 203693765 | | 7/2014 |
| CN | 105748122 | | 7/2016 |
| JP | 2013081563 | | 5/2013 |
| WO | WO-2015110056 A1 * | 7/2015 | ............ A61B 50/36 |
| WO | 2017035474 | | 3/2017 |
| WO | WO-2017035474 A1 * | 3/2017 | ............ A61B 50/36 |
| WO | 2020049325 | | 3/2020 |

OTHER PUBLICATIONS

Lovrec, Vida Gavric, Cokan, Andrej, Lukman, Lara, Arko, Darja, Takac, Iztok; Retained Surgical Needle and Gauze After Cesarean Section and Adnexectomy: A Case Report and Literature Review; Journal of Internal Medical Research, 46(11); pp. 4775-4780; Nov. 2018.

Institute of Medicine, Committee on Quality of Health Care in America, L. Kohn, J. Corrigan, and M. Donaldson, Eds.; To Err is Human: Building a Safer Health System; Washington (DC): National Academies Press; 2000.

Gawande, Atul, Studdert, David, Orav, E. John, Brennan, Troyen, Zinner, Michael; Risk Factors for Retained Instruments and Sponges After Surgery; The New England Journal of Medicine, 348(3); pp. 229-235; Jan. 2003.

Department of Health and Human Services, Office of the Inspector General; Adverse Events in Hospitals: National Incidence Among Medicare Beneficiaries; Nov. 2010; OEI-06-09-00090.

No Thing Left Behind: A National Surgical Patient Safety Project to Prevent Retained Surgical Items; www.nothingleftbehind.org.

The Joint Commission Sentinel Event Alert, 51; retrieved from https://www.jointcommission.org/-/media/tjc/documents/resources/patient-safety-topics/sentinel-event/sea_51_urfos_10_17_13_final.pdf; Oct. 2013.

Cima, Robert, Kollengode, Anantha, Garnatz, Janice, Storsveen, Amy, Weisbrod, Cheryl, Deschamps, Claude; Incidence and Characteristics of Potential and Actual Retained Foreign Object Events in Surgical Patients; Journal of the American College of Surgeons, 207(1); pp. 80-87; Jul. 2008.

PCT Application PCT/US2021/053131, International Search Report & Written Opinion of the International Searching Authority, mailed Jan. 10, 2022.

* cited by examiner

SYSTEM AND METHODS FOR PROVIDING INDUCTIVE SENSING OF SHARPS AND OTHER MEDICAL INSTRUMENTS

CROSS-REFERENCE TO RELATED APPLICATIONS

This application claims priority to U.S. Provisional Application No. 63/086,300, entitled "Intra-Operative Sterile-Field Apparatus, System, and Methods for Detecting and Counting Contaminated Suture Needles," filed Oct. 1, 2020, and U.S. Provisional Application No. 63/195,924, entitled "Intra-Operative Sterile-Field Apparatus, System, and Methods for Detecting and Counting Contaminated Suture Needles," filed Jun. 2, 2021, the entirety of both of which is herein incorporated by reference.

TECHNICAL FIELD

Systems and methods are provided for a medical counting device, software, and computational algorithms suitable for identifying the presence of a surgical needle within the device, counting of the number of needles deployed and used, typically on a sterile field on a patient in any therapeutic or diagnostic setting.

BACKGROUND

In diagnostic and therapeutic areas in a hospital (e.g., an operating room) of a hospital, almost every type of procedure requires a variety of sutures, surgical needles, and other sharp tools and instruments (e.g., scalpel blades, bovie tips, hypodermic needles, staples, wires, and other so-called "sharps"). These items provide a risk of injury to both the patient and others involved in the procedure and the operating room environment. For example, suture needles are sharp and pose an immediate risk of percutaneous puncture or laceration to the surgical staff as the needles and other sharps require manual handling to account for their use and proper disposition in the operating room and other areas where such sharps are utilized. Further, there are medical risks to the patient if needles or other sharps are retained in the patient.

In order to mitigate risk to the patient, surgical staff needs to accurately and statistically verify the number of needles and other sharps that entered the surgical field for potential use, the number of needles and other sharps that were actually used during the surgical procedure, the number of needles and other sharps that were unpacked and placed in the surgical field and the number of total needles and other surgical sharps, used in the procedure+unpacked in the field to be disposed in the appropriate sharps receptacle otherwise known as the "required sharps count."

Oftentimes, the only method available to account for needles and sharps are manual counting methods utilizing, in many instances, manual paper forms white board or similar manual paper tracking chart. Further, accounting for needles and other sharps that are deployed to the surgical field for use and which needles are consumed by the surgical staff during the surgical case are similarly manually undertaken. This manual tracking and counting process typically requires several surgical staff interact directly with needles and other sharps. This current manual process is time-consuming, tedious, laborious, and fraught with potential process defects that subject patients and surgical staff to undue error and injury.

DETAILED DESCRIPTION

Systems and methods are provided for an intra-operative apparatus and system positioned within the aseptic surgical area related to surgical needles. Surgical needle detection and counting methods are also provided.

Systems and methods may provide a counting device and associated software for the operating room environment, and for any environment where needles and sharps might be utilized in diagnostic or therapeutic settings, which can account for and count the number and type of used surgical suture needles that enter the sterile field and captures and counts needles are used during the operation. Further, systems and methods provided herein may include a single repository for other surgical sharps. This may save time and labor and decrease the likelihood for error that is typically caused by manual counting and handling of used surgical needles and other sharps. Furthermore, example processes described herein may eliminate a hand-off step in the workflow between the surgeon and operating room support personnel (typically the scrub tech) when the surgeon is finished with a given suture/needle.

In embodiments, a surgeon (or surgical staff) is able to place a needle directly in the counting apparatus and get positive auditory and visual indication that the needle was accounted for and secured in a safe sharps collection container. Further, the surgical needle collected is able to be displayed on a monitor (e.g., as captured by a camera) visible to the entire surgical team providing further visual confirmation that the surgical needle has been successfully deposited in the counting apparatus. This visual confirmation can support post procedure accounting for used surgical needles. Example systems and methods may be designed to detect surgical needles captured ranging from 5 mm to 60 mm arc length and can discern surgical needle shapes and needle tip characteristics. Example systems may be able to discern multiple needle shapes include a range from ⅜ to ⅝ circle to straight and multi-curve needles. Systems may be designed to detect a range of needle point types, such as, but not limited to, sharp and blunt taper points, cutting and reverse cutting edges. Systems and methods herein may support needle counting in a very wide range of surgical procedures. Certain embodiments may include a tray that includes a repository for other surgical sharps creating a single repository for sharps in the operating room.

Figure 1:
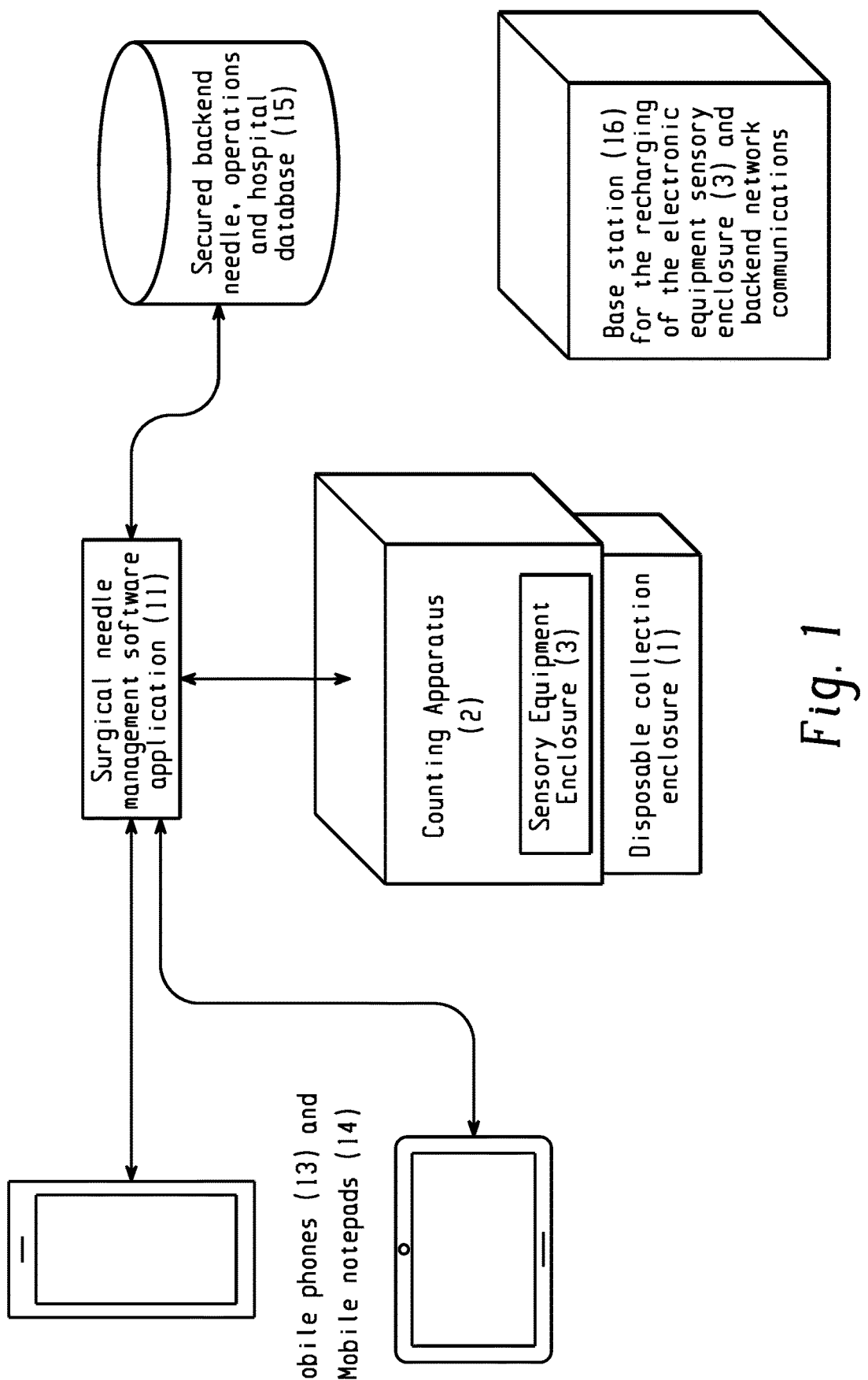
FIG. 1 is a block diagram depicting an integrated counting apparatus having an integrated software that may be used on a sterile platform of an operating room.
Figure 2:
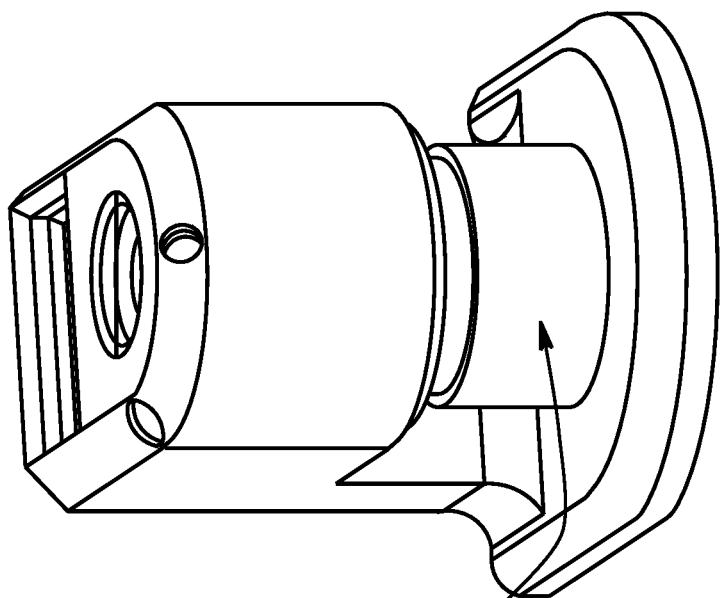
FIG. 2 is a diagram depicting an example form factor for a collecting appliance with a disposable collection enclosure positioned therein.
Figure 2:
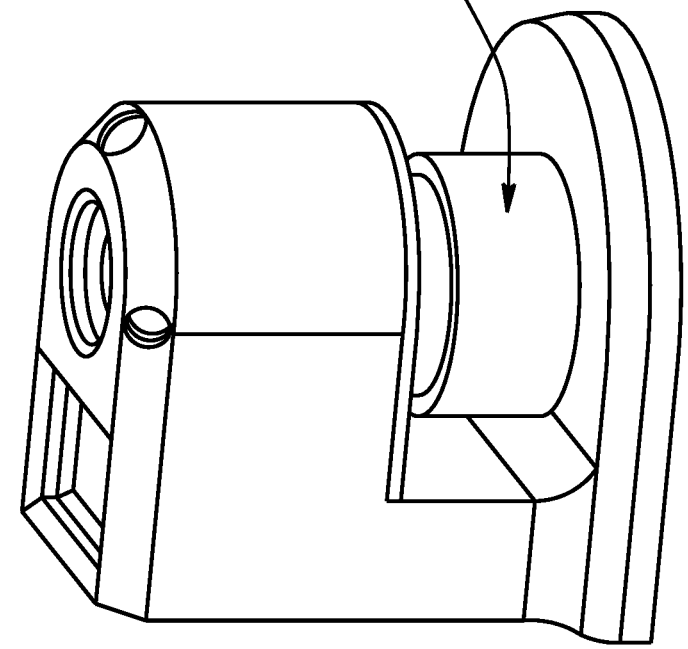

FIG. 1 is a block diagram depicting an integrated counting apparatus having an integrated software that may be used on a sterile platform of an operating room. The apparatus includes a disposable collection enclosure 1, a collecting appliance 2 configured for accommodating the disposable collection enclosure(s) 1. FIG. 2 is a diagram depicting an example form factor for a collecting appliance 2 with a disposable collection enclosure 1 positioned therein.

Figure 3:
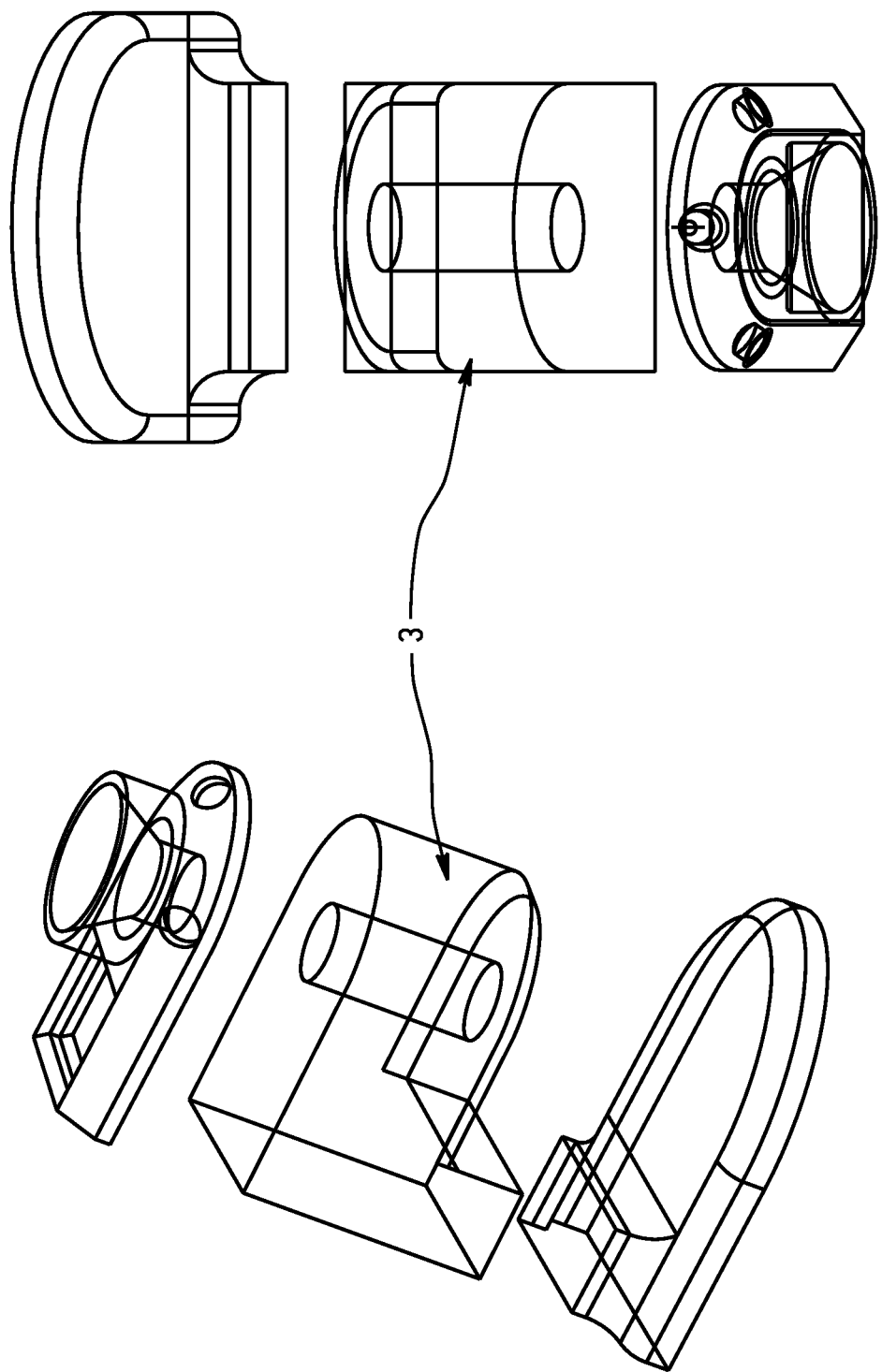
FIG. 3 is a diagram depicting a portion of a housing of an example collecting appliance that forms an electronic sensory equipment enclosure.

With reference back to FIG. 1, the collecting appliance 2 may have an electronic sensory equipment enclosure 3 for sensing surgical suture needles, sharps, or other medical implements after use in a surgical procedure. FIG. 3 is a diagram depicting a portion of a housing of an example collecting appliance 2 that forms an electronic sensory equipment enclosure.

Figure 4:
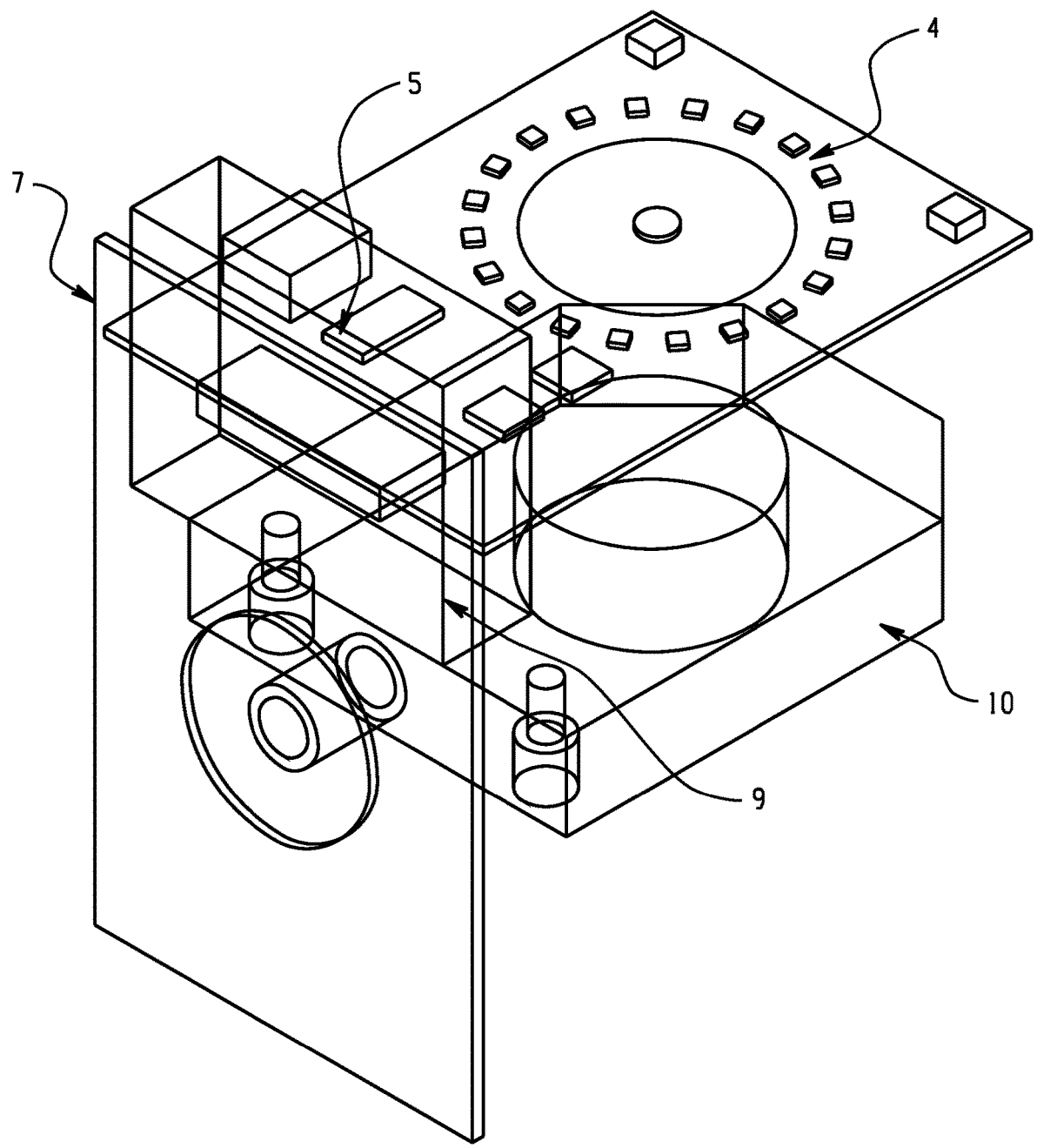
FIG. 4 is a diagram depicting example features of an example electronic sensory equipment enclosure.
Figure 8:
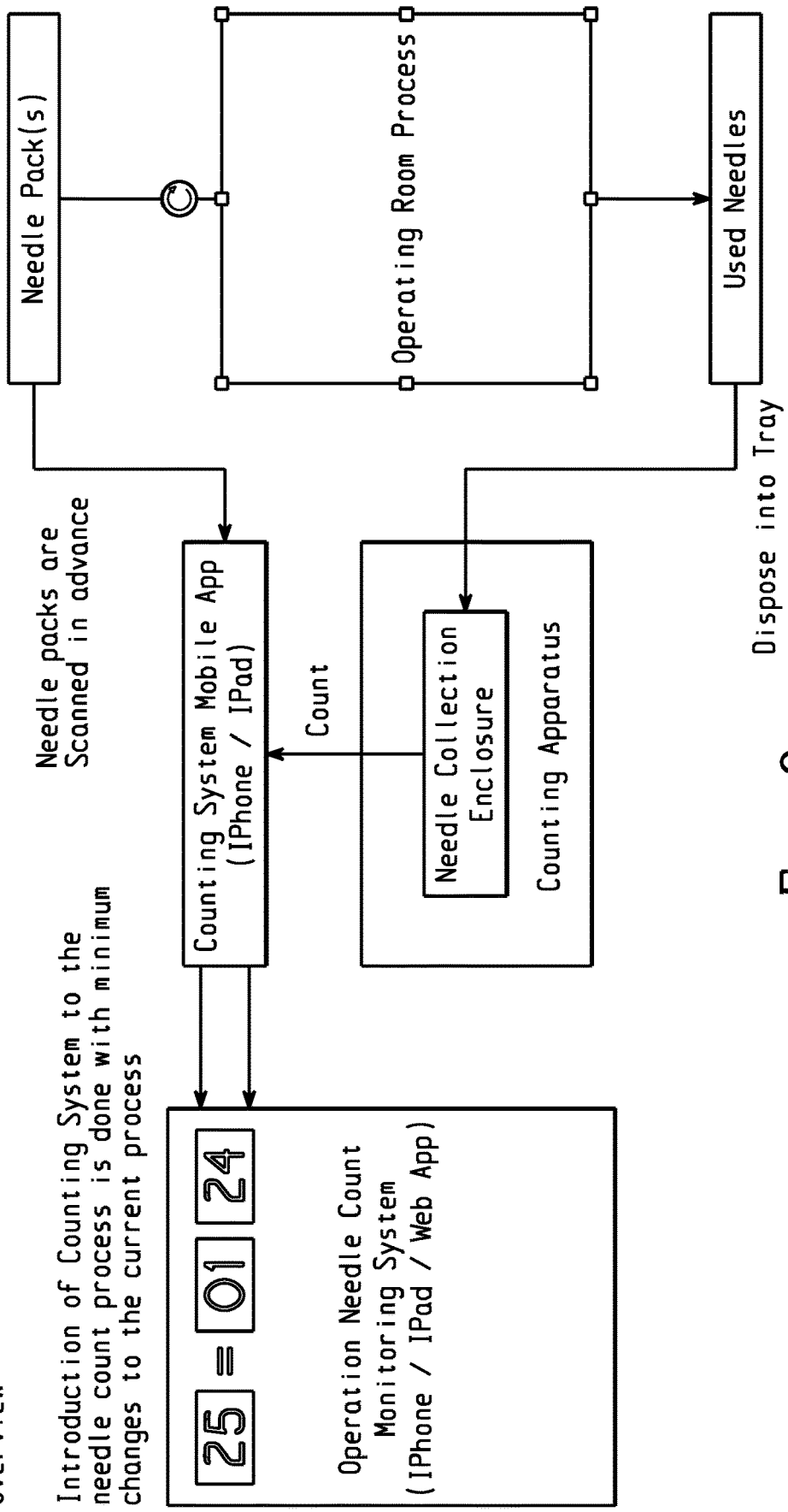
FIG. 8 is a block diagram depicting example general communications, data flow, and output that can be produced by the system when integrated into the current workflow process.
Figure 12:
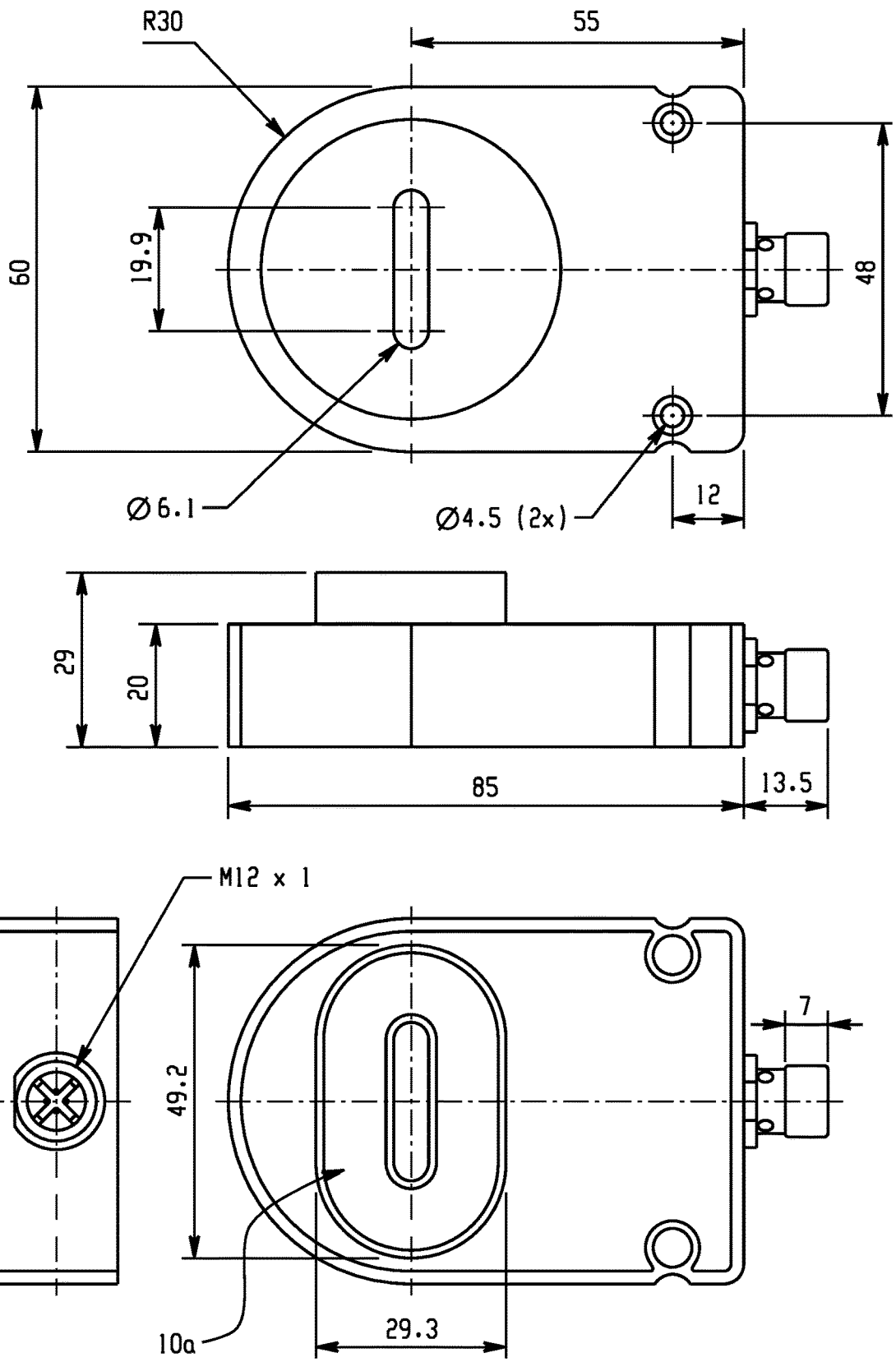
FIG. 12 shows the inductive sensing coil and circuit board in detail in accordance with an embodiment.

The electronic sensory equipment enclosure 3 is installed within the collecting appliance 2 and may include a variety of features. FIG. 4 is a diagram depicting example features of an example electronic sensory equipment enclosure 3. An electronic sensory equipment enclosure 3 may include features such as visual indicators for power and charging level indication and needle detection 4, a speaker 5 for audible detection indication, a power supply 9, a communication circuitry printed circuit board 7 for Blue Tooth and near field communications to a software management platform (e.g., as depicted in FIG. 8), and an inductive sensor(s) or other detecting sensors, such as a metal detecting sensor 10, board 10, and the contained inductive sensor (e.g., as depicted in FIG. 12 at 10a). The sensory equipment 3, the visual indicator or display 4, the speaker, and the needle sensor 10, board 10, and sensor 10a may all be connected to and powered by a rechargeable power supply 9.

In an embodiment, an inductive sensor may be used for detecting items at the end of their use in the surgical procedure. In a simple proximity sensor the device is supplied with electrical power, which causes an alternating current to flow in a coil (sometimes referred to as a loop, spool or winding). When a conductive or magnetically permeable target, such as a steel surgical needle, approaches the coil, this changes the coil's impedance. When a threshold is passed, this acts as a signal that the target is present. Put in other terms, The working principle is based on a coil and oscillator that makes an electromagnetic field in the close environmental factors of the detecting surface. The presence of a metallic object (actuator) in the application area causes dampening of the oscillation amplitude. The ascent or fall of such wavering is distinguished by a threshold circuit that changes the output of the sensor. The working distance of the sensor relies upon the actuator's shape and size and is directly connected to the type of material.

In an embodiment of this design, other design considerations in the inductive sensor include: (1) avoiding circuitry and components that that put out a frequency near the 685 KHz that the sensor coil resonates at, like the boost converter; (2) The inductive sensors delay in the output signal is designed at 150 ms to allow for needles to be dropped through the sensor as frequently as every second; (3) standard inductive sensors usually have a mechanical sensitivity adjustment with a mechanical potentiometer, where this design may include a digit potentiometer adjustment for validation and calibration accuracy; (4) current consumption is kept at a maximum of 15-20 mA in order to maintain battery life during extended operational procedures.

In a simple proximity sensor the device is supplied with electrical power, which causes an alternating current to flow in a coil (sometimes referred to as a loop, spool or winding). When a conductive or magnetically permeable target, such as a steel surgical needle, approaches the coil, this changes the coil's impedance. When a threshold is passed, this acts as a signal that the target is present.

In one embodiment, in order to provide sensitivity of the inductive ring sensor and the sensing of needles as small as 5 mm, systems and methods may utilize an oval opening rather than a circular one in the sensor and an oval shaped funnel that positions the needle material in closer proximity to the oval sensor opening. This can enable the needle material to pass near the sensing device coil to increase sensitivity. Furthermore, flat oval winding may be used to ensure maximum density of the sensing coil versus traditional round wire windings. (10a)

The disposable collection enclosure 1 may manufactured and then stored via a sterilized process using sterilized materials and shipped in sterile packaging. The collecting appliance 2 may be autoclavable. In embodiments, the electronic sensory equipment enclosure 3 can be assembled and disassembled into the sealed collecting appliance 2, sealing the expose sterile collecting appliance 2 before being placed into the surgical field. In embodiments, the removable disposable collection enclosure 1 can be removed and replaced with another disposable collection enclosure 1 in a sterile fashion during the surgical procedure to provide additional capture capacity.

Figure 5:
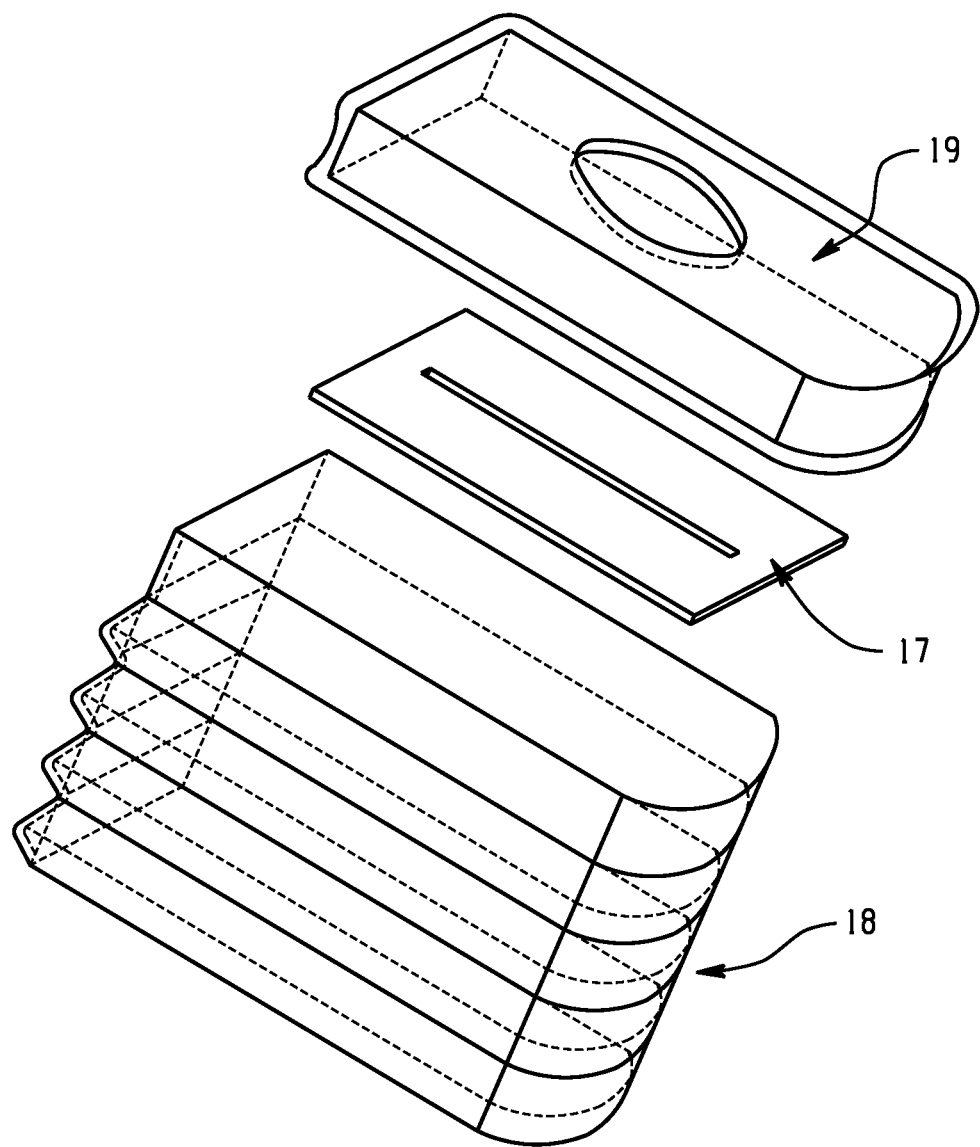
FIG. 5 is a diagram depicting an expandable disposable collection enclosure having self-sealing functionality.

A disposable collection enclosure 1 may take a variety of forms. FIG. 5 is a diagram depicting an expandable disposable collection enclosure having self-sealing functionality. The disposable collection enclosure 1 includes a self-sealing mechanism 17 to retain captured sharps when removed from the collecting appliance 2. In one embodiment the disposable collection enclosure is a sterile disposable receptacle that can expand and collapse 18 via an accordion-shape structure and has a self-sealing interface and cover for temporary attachment to counting device. An example receptacle is made of puncture resistant material, can be expandable to different sizes to store small to large numbers of used/captured needles. In one embodiment, the receptacle is not easy to collapse when filled with needles and will not break easily when dropped (e.g., via a member that moves into place on expansion that inhibits collapse once expanded). In one embodiment, a disposable collection enclosure attaches to the main body of the collecting appliance 2 via a slip fit channel which allows it to remain securely in place but removable when needed for inspection or disposal.

In embodiments, the disposable collection enclosure 1 can conveniently be removed from the collection apparatus 2 and replaced interoperatively with a new disposable collection enclosure 1. The surgical needle management software application 11 may be configured to uniquely track the disposable collection enclosure 1 with a scanned unique id (e.g., a bar code, a QR code, a row or multi-dimensional (2 or more) array of microdots, an ITrace™ mark) for each collection enclosure 1 as designed into the collection apparatus 2. In an embodiment, the unique id is printed on a top surface 19 (e.g., near the enclosure opening of the enclosure shown in FIG. 5) such that it can be read by a scanning device (e.g., an infrared imaging device, a camera) attached to the collecting appliance and pointing down toward the disposable enclosure 1 such that the unique id can be read (e.g., when the disposable collection enclosure is attached to the main body of the collecting appliance 2 via a slip fit channel). Furthermore, the surgical needle management software application 11 tracks the surgical needles that have been prepped in the surgical field for potential surgical usage, through integrated scanning and suture needle identification and storage of the information in the surgical needle usage database 15.

Figure 7:
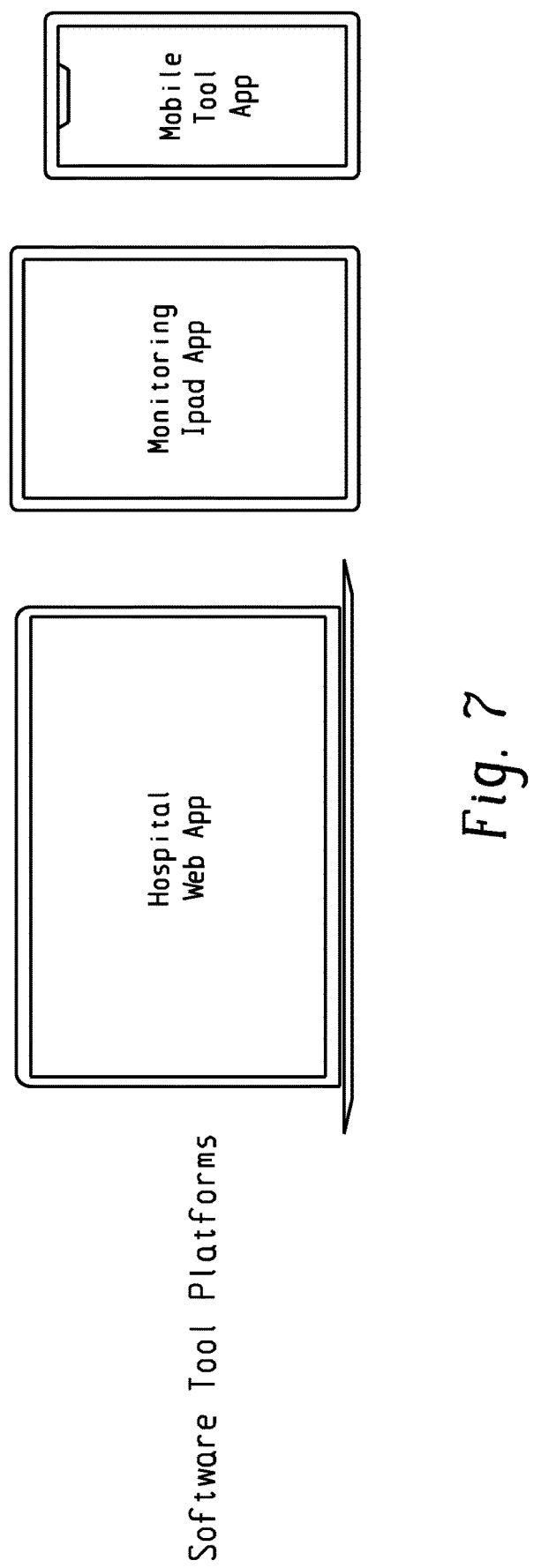
FIG. 7 is a diagram depicting example platforms on which applications that interact with a surgical needle management software application and associated databases.

FIG. 7 is a diagram depicting example platforms on which applications that interact with a surgical needle management software application and associated databases. As depicted in FIG. 7, data may be input to the surgical needle management software application 11 and associated databases 15 and displayed from those sources on a hospital desktop, laptop, or other computing device configured to display reports. The software applications 11 and databases 15 may also interface with mobile phone and other mobile devices operating in the operating room.

Figure 14:
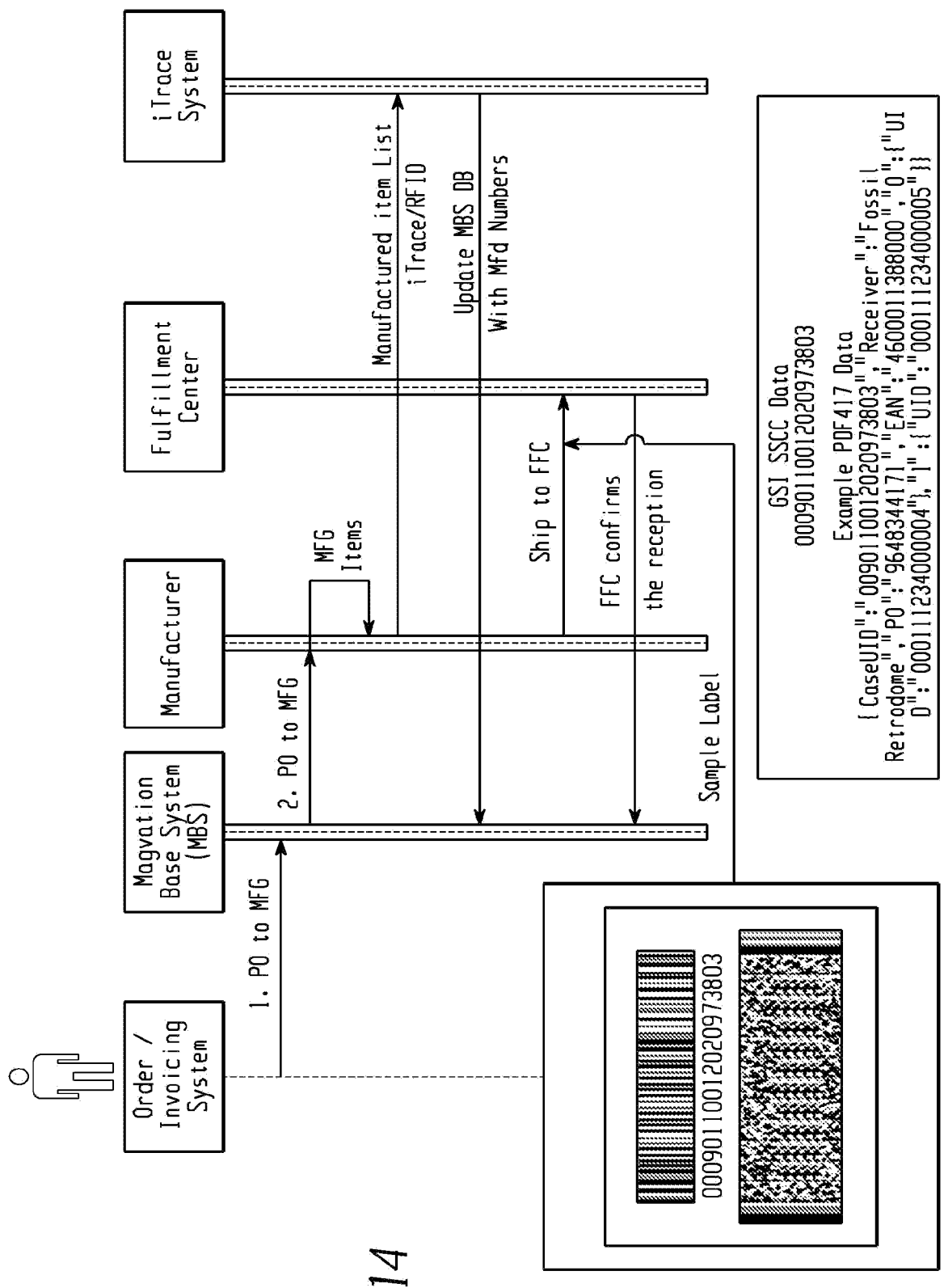
FIG. 14 depicts the Software control of the various components and touchpoints of the Manufacturing process
Figure 15:
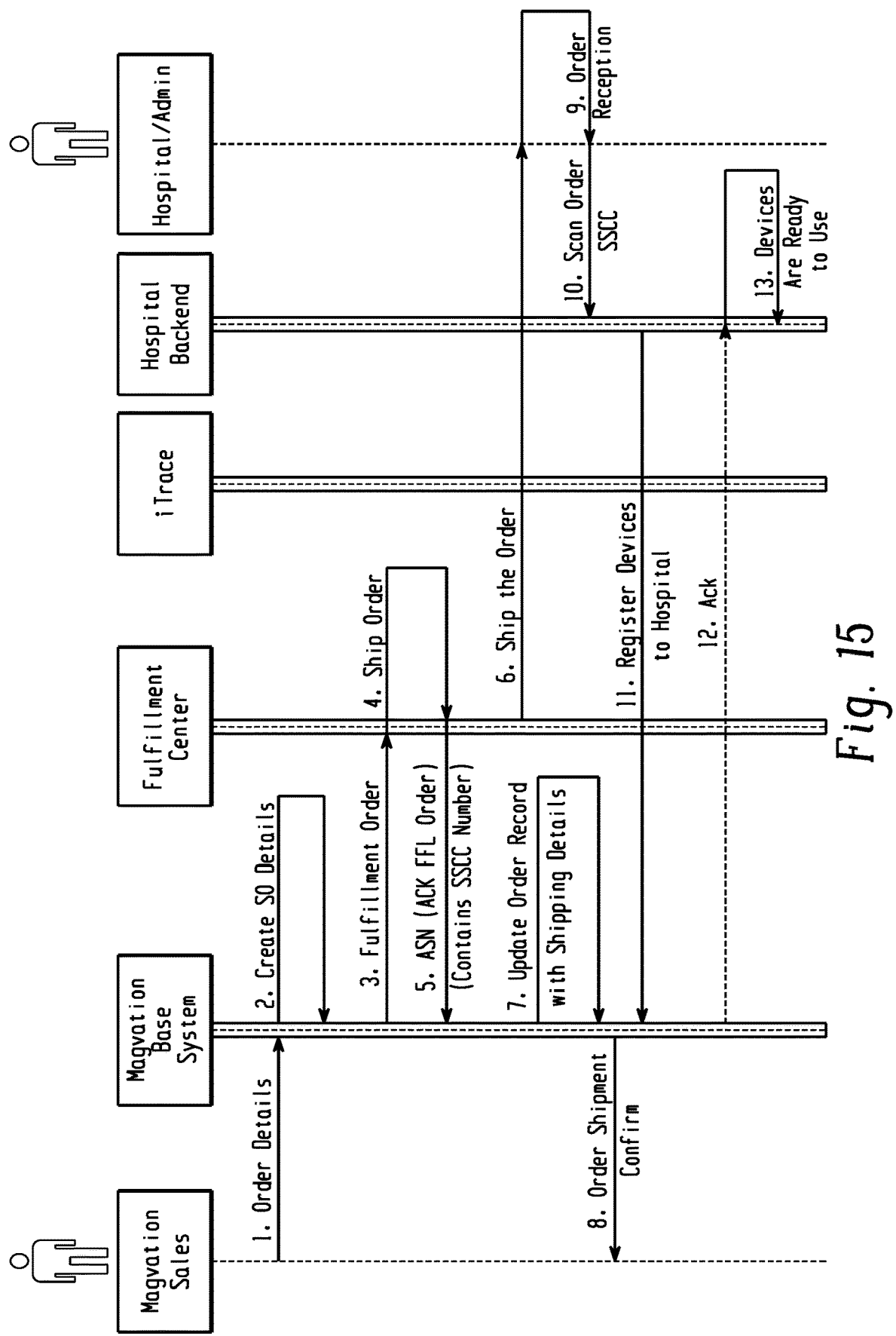
FIG. 15 depicts the Software control of the various components and touchpoints of the Ordering Process and Order Fulfilment Like reference symbols in the various drawings indicate like elements.

Software is provided for support of system functions and the system as a whole. In an embodiment, the software falls into 4 basic groups:
  a. Base Software depicted in FIGS. 14 and 15. This is the main software system which runs on a cloud environment. It is a web-based solution and provides the following base functionalities:
    i. Provides a single place to manage:
      1. Hospitals
      2. Manufacturing facilities
      3. Fulfillment facilities
      4. Orders and Shipment Process
    ii. Allows a manufacturing user to upload item IDs to the manufactured list
    iii. Integration to iTrace backend (Allows mapping of device IDs to iTrace IDs
    iv. Keep track of IDs when manufactured items are received by the Fulfillment centers
    v. Keep track of IDs when items are issued to Hospitals
    vi. Updates the Magvation Hospital System when those items are received by the hospital
    vii. Sync the status of the HayBrains (Integrated Counting Apparatus shown in FIG. 1) that are "Registered" at the Hospitals
    viii. Keeping track of un-identified (counterfeit) Trays
    ix. Provide necessary intelligence to Magvation Administration to counter the use of counterfeit collection trays with the Integrated Counting Apparatus.
  b. Magvation Hospital Software which functions to:
    i. Maintain all the Haybrain and collection tray IDs received by the hospital
    ii. Manage users
    iii. Manage various Operation Theater locations (ORs)
    iv. Manages Operations Templates (Doctor preferences, Operation type preferences, etc)
    v. Manage Operations and Map Templates to various operations
    vi. Keep track of all needle counting data of all operations
    vii. Keep track of all needle counting data of all operations
    viii. Provide reports on needle counting to hospital authorities
    ix. Keep track of all needle counting and tray usages during each operation
    x. Provide necessary compliance related information and process that is necessary at hospitals
    xi. Communicate with Magvation Base Software to received updates on IDs of HayBrains and Trays
    xii. Generate Reports for various Operations (e.g. Needle usage, etc)
  c. Magvation Mobile APP—Sample output is depicted in FIGS. 8-11. The mobile app will:
    i. Allow to pairing with a HayBrain with NFC tag and BLE pairing
    ii. Run testing procedures for HayBrains (i.e. Communication Testing and Counting Testing)
    iii. Initiate and run registration process to register HayBrains to use at Operation Theaters
    iv. Keep track of all needle counting in each HayBrain unit during an operation
    v. Keep track of all the IDs of the Trays used with HayBrain units during an operation
    vi. Keep track of all the needles allocated for an operation as well as the needles used
    vii. Allow theater staff to run intermediate "Sharps Counts" procedures during an operation and displaying information to the user including, but not limited to, needles scanned, needles captured, expected needles remaining, and counts of needles captured in removed collection trays
    viii. Complete a final "Sharps Count" at the end of an operation and provide final needle counting information
    ix. Allows users to add resources to an Operation using various scanning options (Needles, Trays, etc)
    x. Only one operation at a time can be managed with using HM APP
    xi. Each HM APP is capable of communicating with up to the total number of HayBrains allowed by BLE. Those devices could be used for a given operation. The HM APP will enable OR staff to do necessary interactions with HayBrains (Integrated Counting device)
  d. Magvation Tool APP (Generic iPhone app for Scanning purposes). This APP will:
    i. Provide additional support to OR staff to remotely select required HayBrain units in an OR.
    ii. Allow OR staff to identify needle packs and its counts and keep them on reserve status inside the OR for a given operation iii. Allow OR staff to transfer any needle packs to "In Use" status during any given operation iv. Allow OR staff or other technicians to run a REGISTRATION process of HayBrains at the hospitals v. Has options to scan various GS1 codes (as shown in FIG. 14) to identify the Trays allocated for operation and move them to a sterilized area (e.g., the back table or mayo stand) during operation FIG. 8 is a block diagram depicting example general communications, data flow, and output that can be produced by the system when integrated into the current workflow process.

Figure 9:
FIG. 9 is a block diagram example depicting functions of the software are invoked to assign needles, a specific needle collecting tray, and a specific integrated counting apparatus to a specific operation.
Figure 9:
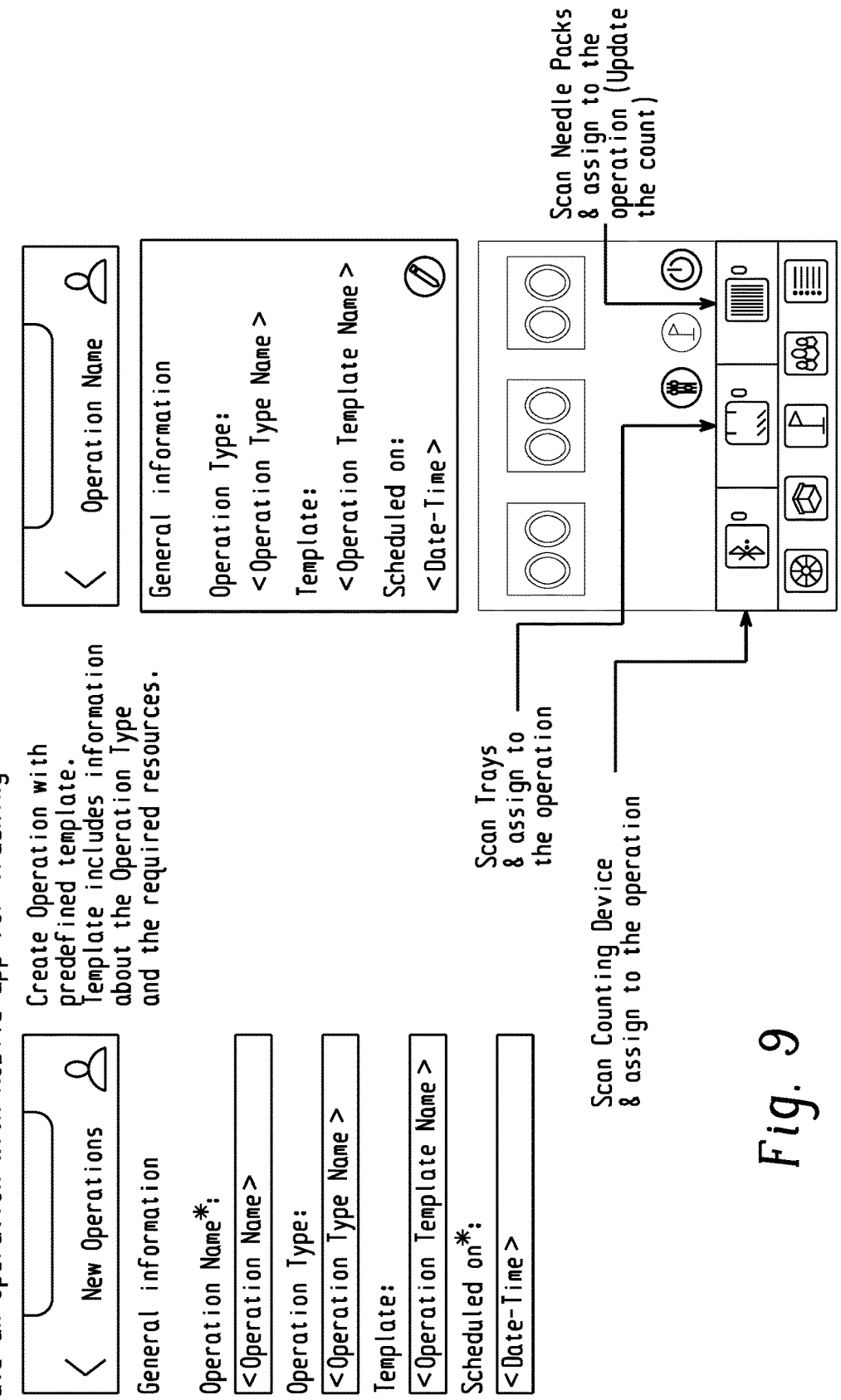

FIG. 9 is a block diagram example depicting functions of the software are invoked to assign needles, a specific needle collecting tray, and a specific integrated counting apparatus to a specific operation.

Figure 10:
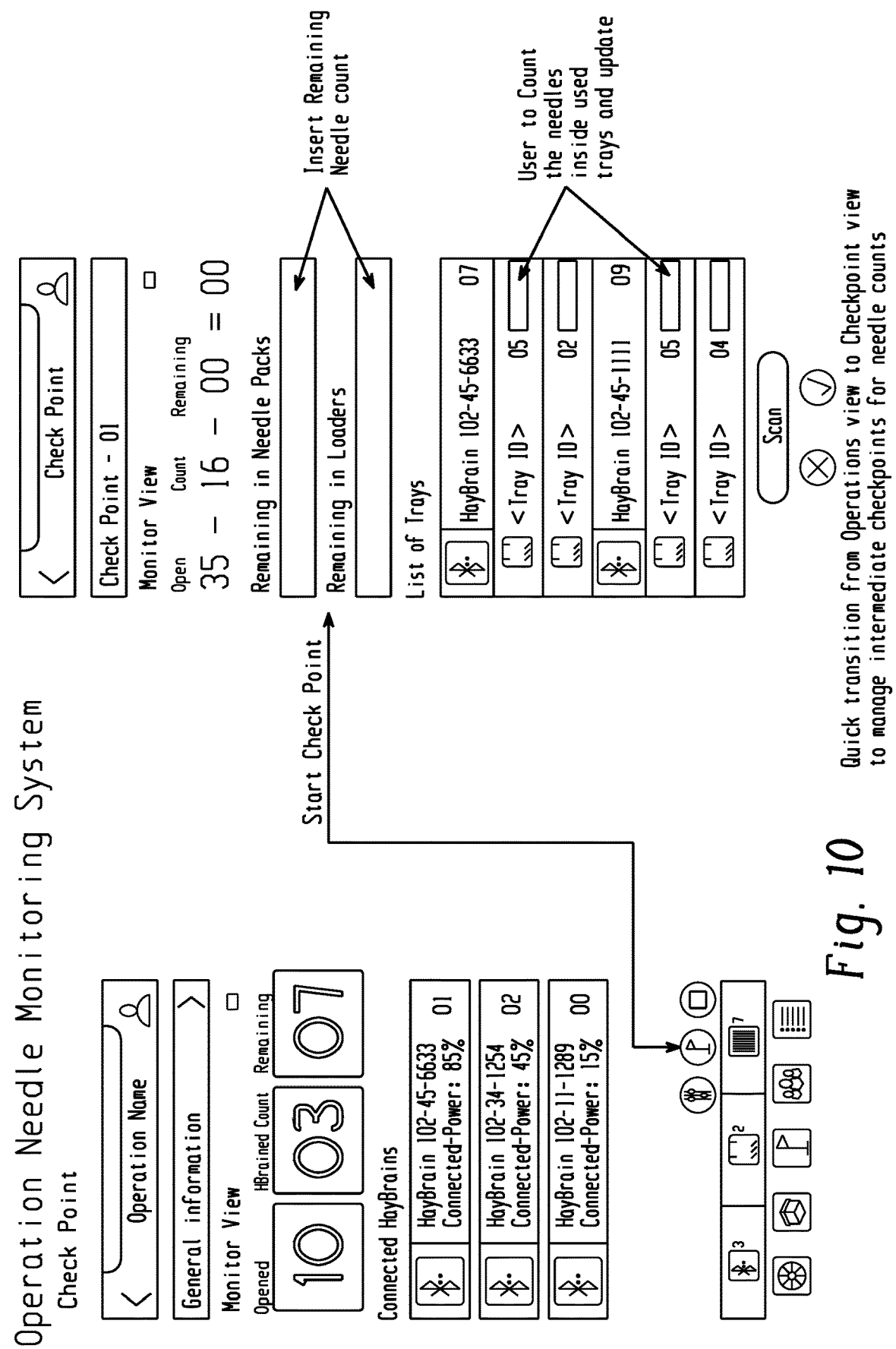
FIG. 10 is a block diagram example depicting functions of the software utilized during a formal needle count, at any time during the operative case to manually enter remaining unused needles, and to adjust the count if needed if a discrepancy is noted with a visual count or to account for needles not used but contaminated (e.g., dropped on the floor).

FIG. 10 is a block diagram example depicting functions of the software utilized during a formal needle count, at any time during the operative case to manually enter remaining unused needles, and to adjust the count if needed if a discrepancy is noted with a visual count or to account for needles not used but contaminated (e.g., dropped on the floor).

Figure 11:
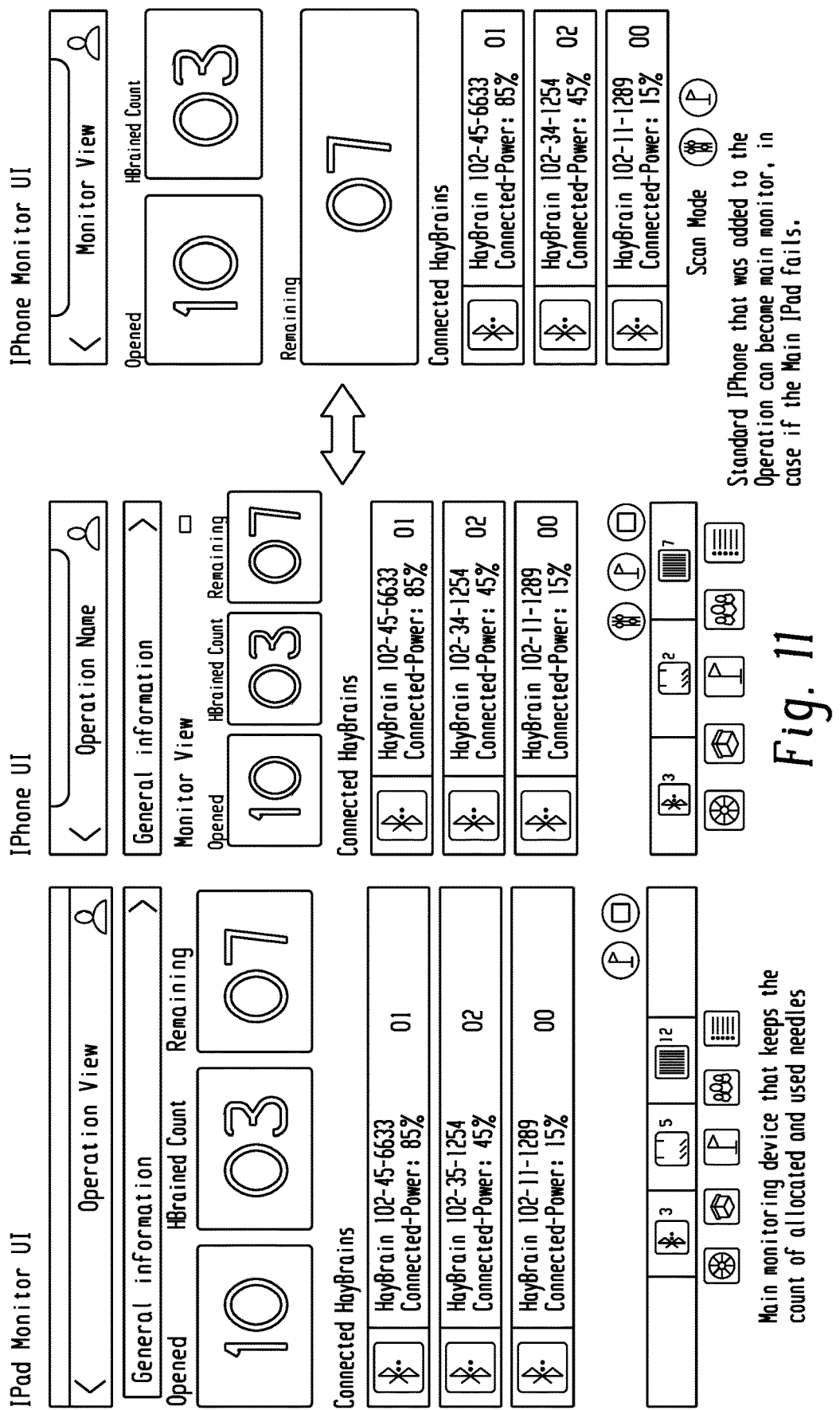
FIG. 11 shows example outputs of needle counts and other information presented to the user during operation.

FIG. 11 shows example outputs of needle counts and other information presented to the user during operation. This same information is available across all user interfaces. Key data displayed include counts of needles scanned into the software at any time of the operation, counts of used needles dropped through the inductive sensor, and expected remaining needles Additionally shown are counts of needles in trays that have been assigned/used in the operation and removed/replaced during the operation.

FIG. 12 shows the inductive sensing coil and circuit board in more detail.

Figure 13:
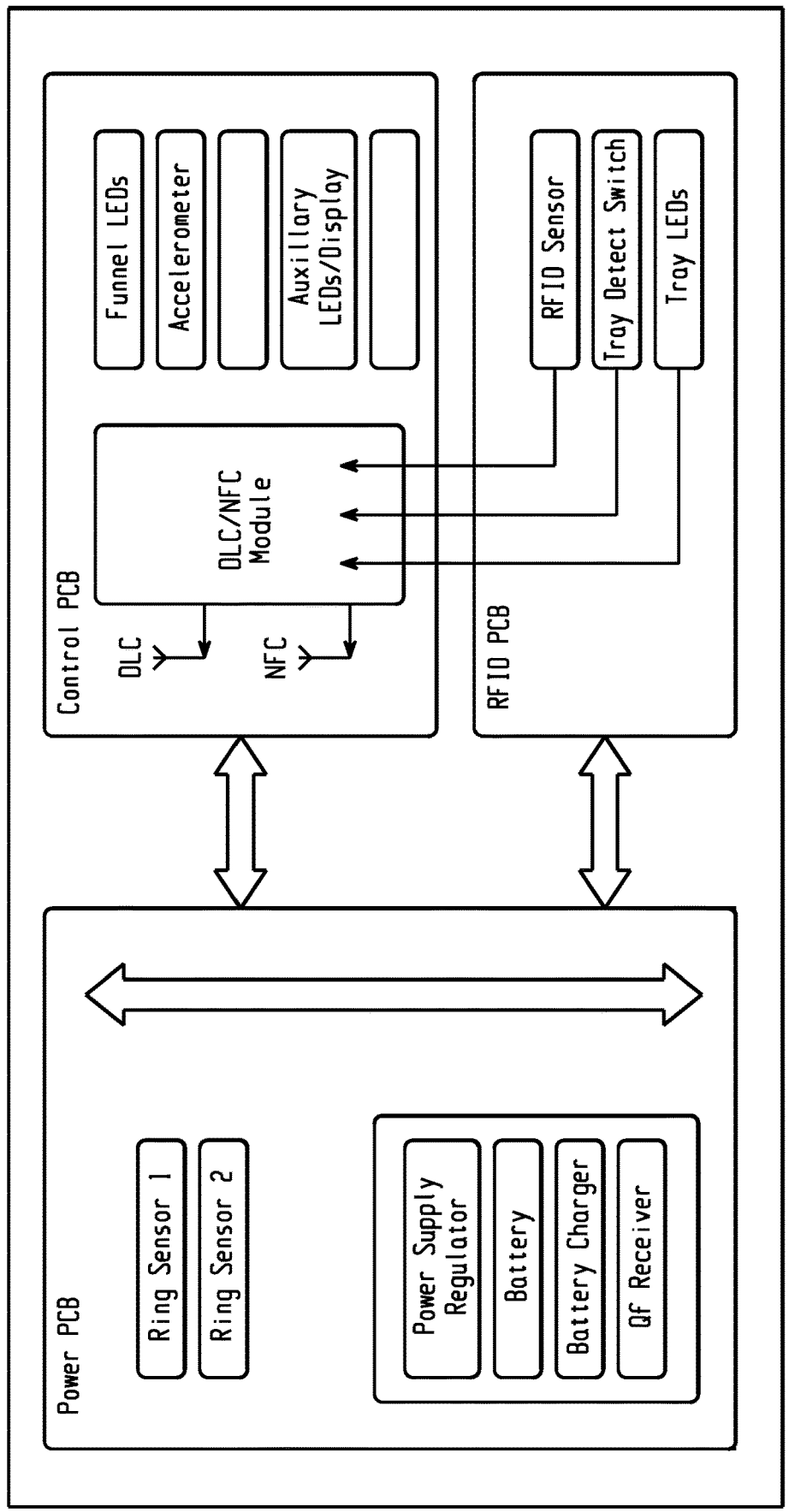
FIG. 13 shows a block diagram of example printed circuit board functions, relations, and communications.

FIG. 13 shows a block diagram of the printed circuit board functions, relations, and communications.

Figure 6:
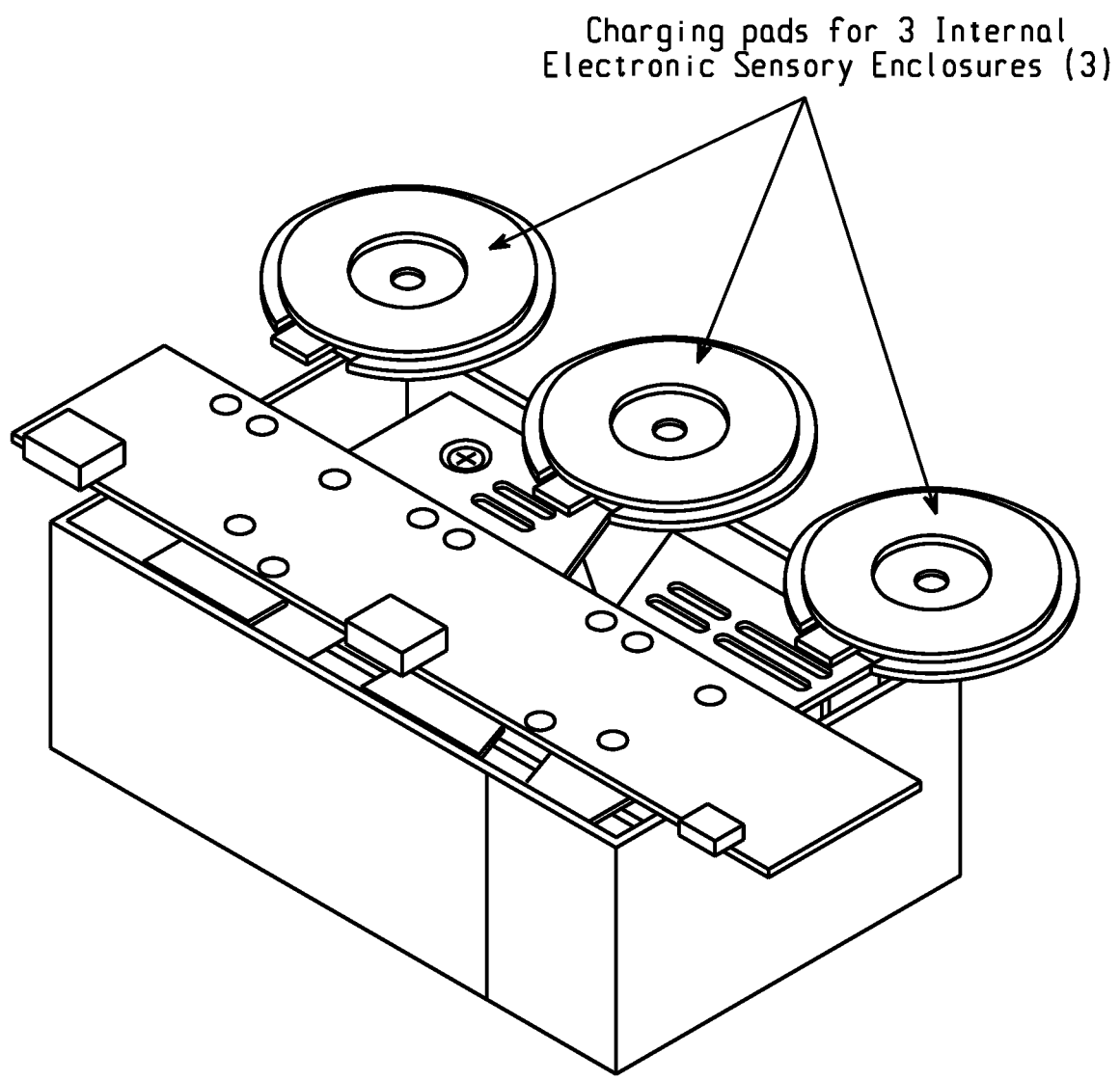
FIG. 6 is a diagram depicting an example base station for recharging one or more electronic sensory equipment enclosures.

Systems and methods as described herein may further include a base station 16 for the recharging of the electronic equipment sensory enclosure 3. In embodiments, the base station 16 may further provide system routing functionality to facilitate system communications. FIG. 6 is a diagram depicting an example base station for recharging one or more electronic sensory equipment enclosures 16. The base station includes charging pads onto which one or more electronic sensory equipment enclosures 3 can be placed so as to charge those components (e.g., by wired charging or wireless (e.g., inductive) charging mechanisms).

The electronic sensory equipment enclosure sterile field collecting appliance 2 communicates to a surgical needle management software application 11, which may be running within the operating room or in a remote location. The application 11 collects needle count information as gathered by the collecting appliance 2 and the internal sensor equipment 3, reflecting this data in a surgical needle usage database 12 per operational procedure. The surgical needle management software application 11 may be configured to interact with applications executing on secured mobile devices 13 and mobile notepads 14. The software application 11 may store data on a secured backend database 15. The surgical needle management software application 11 may also be configured to track the usage of the surgical needle collection enclosure(s) 1 used in the procedure and provides visual usage and needle counts entering the field and placed in the collecting appliance 2 after surgical use. This information may be displayed on the mobile devices 13 and mobile notepads 14 that are paired with the management software application 11. In embodiments, needle counts that are automatically provided by the integral collecting/sensing apparatus may be corrected through manual intervention on the mobile device 13 and mobile notepad 14 through the surgical needle management software application 11, further improving accuracy. Data regarding surgical needle counts collected during an operation may be stored in the secured backend database 15 in a persistent manner. In certain embodiments the surgical needle management software application 11 may be configured to operate effectively to continue counting surgical implements without a connection to the backend database 15, such that service is not interrupted in the event of a communication, power, or other apparatus, however the procedure and needle counting does not require this backend connection for the collecting appliance.

Systems and methods as described herein may further include an operating room counting device wherein once a new disposable needle closure is attached to the counting appliance/apparatus, the apparatus and system are able to detect the attachment of a new collection enclosure and close the count for the previous enclosure. This information is passed to the mobile device application and backend database.

In another embodiment, there is intelligent sampling logic used to enable the use of multiple sensors for detection to ensure accuracy but with appropriate algorithms to prevent double counting a single needle passing through the apparatus.

A number of solutions were researched to detect and count an item as small as a succor needle, 5 mm to 30 mm, varying in shape, diameter and potentially coated and moist with blood or moisture from the patient. One of the attempted methods included experimenting with hydrophobic coating in the inside of the funnel to ensure the needle passes all the way through funnel.

Patient Safety, in the form currently deployed in the healthcare setting, is an outgrowth of the seminal 1999 Institute of Medicine Report: "To Err is Human: Building a Safer Health System." This publication represented the first time that the scope and consequences of medical error was quantified. ("To Err is Human: Building a Safer Health System;" Kohn K T, Corrigan J M, Donaldson M S, eds. Washington, DC: Committee on Quality Health Care in America, Institute of Medicine: National Academy Press; 1999.) Over a decade later, the Office of the Inspector General of the United States published an estimate of the national incidence of adverse events for hospitalized Medicare beneficiaries. (Adverse Events in Hospitals: National Incidence Among Medicare Beneficiaries; Department of Health and Human Services, Office of the Inspector General, November 2010; OEI-06-09-00090.) This report revealed "temporary harm events" befell 13.5% of Medicare beneficiaries during their hospital stay, 44% of which were "clearly or likely Preventable".

The OIG report was followed on 19 Jan. 2009 by the "Patient Safety Rule" (See 42 CFR Part 3 (73 FR 70732)) which codified regulations originally delivered in the Patient Safety and Quality Improvement Act of 2005. (Public Law 109-41-Jul. 29, 2005.) These changes in the way hospital safety were quantified, measured, and regulated ushered in a new era of attention to medical errors.

Specific to the operating room environment, Dr Verna Gibbs, a thoracic surgeon at The University of California, San Francisco, authored In October of 2004, a document called "No Thing Left Behind" (updated in 2018) has become a compendium of accounting processes for surgical items. ("No Thing Left Behind®: A National surgical patient safety project to prevent retained surgical items" www.nothingleftbehind.org (accessed 27 Mar. 2021).) Further evidence of the scope of the surgical items handling issues in the operating room is found in the 17 Oct. 2013 Joint Commission Sentinel Event Alert that described 722 incidents of URFO (Unintentionally Retained Foreign Objects), identified 16 deaths and costs of between $160,000.00 and $200,000.00 per incident. (The Joint Commission Sentinel Event Alert; Issue 51, Oct. 17, 2013; https://www.jointcommission.org/-/media/tjc/documents/resources/patient-safety-topics/sentinel-event/sea_51_urfos_10_17_13_final.pdf (accessed 27 Mar. 2021).) The Joint Commission publication further outlined a prescriptive methodology for counting procedures, wound opening and closing procedures, and identified indications for intra-operative radiographs. Yet, despite the attention paid to processes, the introduction of financial penalties, and detailed reporting requirements, accidental retention of foreign bodies, or Retained Surgical Items (RSI), occurs in approximately 1 of every 1000-1500 operations. (Gavrić Lovrec V, Cokan A, Lukman L, Arko D, Takač I. Retained surgical needle and gauze after cesarean section and adnexectomy: a case report and literature review. J Int Med Res. 2018; 46 (11):4775-80.)

Although a large share of attention is directed toward retained surgical sponges and retained surgical instruments, retained suture-needles and suture-needlesticks are substantive problems that result in injury, morbidity, medicolegal impairments, and even mortality. (Gawande A A, Studdert D M, Orav E J, Brennan T A, Zinner M J. Risk factors for retained instruments and sponges after surgery. N Engl J Med. 2003; 348 (3):229-35.) The National Quality Foundation estimated in 2017, that there were 51 million operations/procedures performed at non-federal hospitals in the US, and in 2019 there were 67 million surgical outpatient procedures performed in ambulatory surgical centers. By a conservative estimate, suture-needle miscounts occur in 4% of operations, suture-needlesticks in 0.5%, suture-needle retention in 0.06%. Assuming an even more conservative estimate that only 50% of the 134,000,000 operations/procedures utilize suture-needles, there are roughly 2,780,000 needle miscount incidents, 335,000 needlestick incidents and 40,000 needle retention incidents per year. Being extremely conservative, if those incidents rates are cut in half, and then halved again, this still represents 788,000 suture-needle incidents per year, all with potentially tragic patient outcomes and potentially material financial consequences.

Issues with needles, needle handling and needle sticks are still the problem, despite the increased attention paid to RSI, the initiation, and adoption of processes intended to mitigate risk to patients and staff. The risk incumbent to staff and patients persists. Under-reporting of retained foreign objects and so-called "near misses" have been found to be significantly underreported and manual counting methods such as those proposed and implemented by No Thing Left Behind and the Joint Commission have proven largely inaccurate. (Cima R R, Kollengode A, Garnatz J, Storsveen A, Weisbrod C, Deschamps C., Incidence and Characteristics of Potential and Actual Retained Foreign Object Events in Surgical Patients. J Am Coll Surg. 2008; 207 (1):80-87.)

The problem with needles and sharps in general in the operating room garnered sufficient attention to prompt the Association of periOperative Registered Nurses ("AORN"), a policy making body representing nursing staff in the operating room, to provide, for public comment, a new set of recommendations entitled "Guideline for Prevention of Unintentionally Retained Surgical Items". Material to this invention, AORN includes, among their recommendations, " . . . use an adjunct technology device to verify the location of surgical [supplies] or the outcome of manual counting procedures, when possible". The direct reference to "adjunct technology" represents a tacit acknowledgement on AORN's part that current policies and processes for counting, accounting, and disposal of needles and other surgical sharps (as well as sponges and other so-called "soft goods") in the operating room are inadequate protections for staff and patients alike.

Through systems and methods described herein, all suture needles entering the sterile field for prep and all needles used in the surgery are accounted for and tracked. In an embodiment, during an operation, the surgical needle management software application 11 and its integration with scanning application of the mobile devices and the automatically captured needle sensing of the collection apparatus 2, captures the open needle packages placed into in the sterile field and the surgically used needle count, as the surgeon drops the used needle into the collection apparatus 2. This can enable assured accounting of all surgical needles in the sterile field. The benefits are assurances that needles have not been left in the patient before closure and that needles are not left on the surgical floor, risking medical staff health. This process is safer and more efficient than the current practice of manually counting suture needles at the close of the operation. Furthermore, once the operation is closed, the collection enclosures 1 can be disposed safely in the appropriate sharps' repository assuring safety of medical staff infection and sticks from sharps. In addition, the present invention provides accuracy and automation efficiencies in the closure process of an operating procedure. This patient centered focus reduces risk to both the patient and operating staff, reduces unnecessary anesthesia time while searching for supposedly missing needles, reduces other costs and time in completing the surgical procedure, and ultimately shortens the turnover time for use of the operating room.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system can include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, can include machine instructions for a programmable processor, and/or can be implemented in a high-level procedural language, an object-oriented programming language, a functional programming language, a logical programming language, and/or in assembly/machine language. As used herein, the term "computer-readable medium" refers to any computer program product, apparatus and/or device, such as for example magnetic discs, optical disks, solid-state storage devices, memory, and Programmable Logic Devices (PLDs), used to provide machine instructions and/or data to a programmable data processor, including a machine-readable medium that receives machine instructions as a computer-readable signal. The term "computer-readable signal" refers to any signal used to provide machine instructions and/or data to a programmable data processor. The computer-readable medium can store such machine instructions non-transitorily, such as for example as would a non-transient solid-state memory or a magnetic hard drive or any equivalent storage medium. The computer-readable medium can alternatively or additionally store such machine instructions in a transient manner, such as for example as would a processor cache or other random access memory associated with one or more physical processor cores.

The computer components, software modules, functions, data stores and data structures described herein can be connected directly or indirectly to each other in order to allow the flow of data needed for their operations. It is also noted that a module or processor includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality can be located on a single computer or distributed across multiple computers depending upon the situation at hand.

In the descriptions above and in the claims, phrases such as "at least one of" or "one or more of" can occur followed by a conjunctive list of elements or features. The term "and/or" can also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

For example, the systems and methods may include data signals conveyed via networks (e.g., local area network, wide area network, internet, combinations thereof, etc.), fiber optic medium, carrier waves, wireless networks, etc. for communication with one or more data processing devices. The data signals can carry any or all of the data disclosed herein that is provided to or from a device.

Additionally, the methods and systems described herein may be implemented on many different types of processing devices by program code comprising program instructions that are executable by the device processing subsystem. The software program instructions may include source code, object code, machine code, or any other stored data that is operable to cause a processing system to perform the methods and operations described herein. Other implementations may also be used, however, such as firmware or even appropriately designed hardware configured to carry out the methods and systems described herein.

The systems' and methods' data (e.g., associations, mappings, data input, data output, intermediate data results, final data results, etc.) may be stored and implemented in one or more different types of non-transitory computer-readable storage medium that is stored at a single location or distributed across multiple locations. The medium can include computer-implemented data stores, such as different types of storage devices and programming constructs (e.g., RAM, ROM, Flash memory, flat files, databases, programming data structures, programming variables, IF-THEN (or similar type) statement constructs, etc.). It is noted that data structures describe formats for use in organizing and storing data in databases, programs, memory, or other computer-readable media for use by a computer program.

The systems and methods may be provided on many different types of computer-readable media including computer storage mechanisms (e.g., CD-ROM, diskette, RAM, flash memory, computer's hard drive, etc.) that contain instructions (e.g., software) for use in execution by a processor to perform the methods' operations and implement the systems described herein.

The computer components, software modules, functions, data stores and data structures described herein may be connected directly or indirectly to each other in order to allow the flow of data needed for their operations. It is also noted that a module or processor includes but is not limited to a unit of code that performs a software operation, and can be implemented for example, as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Finally, as used in the description herein and throughout the claims that follow, the meanings of "and" and "or" include both the conjunctive and disjunctive and may be used interchangeably unless the context expressly dictates otherwise; the phrase "exclusive or" may be used to indicate situation where only the disjunctive meaning may apply.

The invention claimed is:

1. A surgical needle counting system for an operating room, comprising:
    a counting apparatus;
    a removable collecting enclosure positioned at an exit of the counting apparatus;
    wherein the counting apparatus includes a sensor for sensing a surgical needle when it is dropped into the counting apparatus, the counting apparatus being configured for storing a number of counted surgical needles;
    wherein the counting apparatus is configured to detect removal of the removable collecting enclosure and attachment of a new removable collecting enclosure and to close a count associated with the number of counted surgical needles in the removed removable collecting enclosure;
    wherein when a new removable collecting enclosure is attached to the counting apparatus, the closed count and an identification of the new removable collecting enclosure is transmitted to a backend database.

2. The system of claim 1, wherein once a needle is sensed as having been deposited in the counting apparatus, the deposited needle count is increased by one and a visible or audible signal is provided.

3. The system of claim 1, wherein once a needle is sensed as having been deposited in the counting apparatus, the deposited needle count is increased by one and stored in an electronic memory to track total needle usage for the operation.

4. The system of claim 3, wherein wireless or near field communication is used to provide an updated count to a registered mobile device in the operating room.

5. The system of claim 1, wherein the deposited needle count is transmitted to a secure remote database for tracking and storing the operations needle usage.

6. The system of claim 1, wherein the closed count and the identification of the new removable collecting enclosure is transmitted to a mobile device application.

7. The system of claim 1, wherein a deposited needle count is transmitted to a remote database, where a local deposited needle count is maintained in case of communication failure or failure of a user interface device, wherein upon restoration of communication or the user interface device, the local deposited needle count is transmitted to the remote database.

8. The system of claim 1, wherein when a deposited needle count threshold is reached, the counting apparatus provides an audible or visual signal to replace the removable collecting enclosure with another, wherein the deposited needle count for the removable collecting enclosure is transmitted to a remote database.

9. The system of claim 1, wherein the counting apparatus is configured to track a number of needles and needle types that have been introduced into a sterile operating field for potential use and stores and provides an introduced needle metric to a mobile device application.

10. The system of claim 9, wherein the counting apparatus is configured to reconcile the deposited needle count with the introduced needle metric.

11. The system of claim 1, wherein the sensor is of an infrared type, an electromagnetic type, an acoustic wave type, a visual image type, or a pressure sensing type.

12. The system of claim 1, wherein the removable collecting enclosure comprises a magnet attached to a bottom surface.

13. The system of claim 1, further comprising a hub for wirelessly charging the counting apparatus.

14. The system of claim 1, further comprising a camera configured to take a picture inside of the removable collecting enclosure to provide a source for a backup count, wherein the picture is transmitted to and stored in a remote database, wherein the picture is transmitted to and displayed on a mobile device.

15. The system of claim 14, wherein a processor is configured to perform image recognition on the picture to determine a backup count value that is compared to a deposited needle count determined using the sensor.

16. The system of claim 1, further comprising a user interface for receipt of a manual count adjustment.

17. The system of claim 1, wherein the removable collecting enclosure is collapsible/expandable and self-sealing, wherein the removable collecting enclosure is configured for expansion in the operating room prior to connection to the counting apparatus, wherein said self-sealing is configured to prevent needles therein from exposure including when the removable collecting enclosure is dropped.

18. The system of claim 1, wherein the removable collecting enclosure includes a magnet in a base portion for attracting needles deposited therein.

19. The system of claim 1, wherein the sensor comprises multiple sensors, wherein the system includes logic for preventing double counting of a needle based on signals provided by the multiple sensors.

20. The system of claim 1, further comprising an intake funnel coated with hydro-phobic material configured to guide a needle through the sensor and into the removable collecting enclosure.

21. The system of claim 1, wherein the counting apparatus further includes a scanner for scanning open surgical needle packages, the counting apparatus being configured for tracking a number of surgical needles associated with the scanned needle packages during operation, wherein the counting apparatus is further configured to compare the number of needles associated with the scanned needle packages with the number of needles dropped into the counting apparatus.

* * * * *